United States Patent
Combe et al.

(10) Patent No.: US 6,291,039 B1
(45) Date of Patent: Sep. 18, 2001

(54) RUFFLING SLIDE AND METHOD FOR MAKING SAME

(75) Inventors: Robert Combe; Serge Moulin, both of Sury le Comtal (FR)

(73) Assignee: Cera France Compagnie d'Equipment Robotique Appliquee, Villars (FR)

(*) Notice: Subject to any disclaimer, the term of this patent is extended or adjusted under 35 U.S.C. 154(b) by 0 days.

(21) Appl. No.: 09/147,030

(22) PCT Filed: Mar. 14, 1997

(86) PCT No.: PCT/FR97/00470

§ 371 Date: Mar. 17, 1999

§ 102(e) Date: Mar. 17, 1999

(87) PCT Pub. No.: WO97/34506

PCT Pub. Date: Sep. 25, 1997

(30) Foreign Application Priority Data

Mar. 15, 1996 (FR) .................................... 96 03548

(51) Int. Cl.$^7$ ................ B32B 31/20; B32B 3/06
(52) U.S. Cl. ............... 428/35.2; 428/36.9; 428/197; 428/198; 156/164; 156/201; 156/204; 156/229; 156/290; 156/308.4; 156/495; 156/553; 2/338
(58) Field of Search ............... 604/385.2; 428/198, 428/196, 197, 200, 36.9, 36.91, 35.7, 35.2; 2/338, 237, 221; 66/190, 192, 202; 156/164, 229, 161, 163, 201, 204, 308.4, 290, 494, 495, 553

(56) References Cited

U.S. PATENT DOCUMENTS 5,209,801 * 5/1993 Smith ................................. 156/161

FOREIGN PATENT DOCUMENTS

2532337 * 3/1984 (FR) .

* cited by examiner

*Primary Examiner*—Rena L. Dye
(74) *Attorney, Agent, or Firm*—Bacon & Thomas PLLC

(57) ABSTRACT

A ruffling slide for making articles with stretchable portions includes a tubular sleeve for containing at least one resiliently elastic yarn element connecting the portions transversely provided on the sleeve and space apart in such a way that they define tubular ruffling sections. The connecting portions also form narrowed portions for locally clamping the elastic yarn elements. The yarn element inserts into the sleeve and is clamped at the narrowed portions in such a way that it extends freely through each tubular section and is movable therein between two positions, i.e., an inoperative position and an operative position in which said element is shorter than the section in question, whereby it may subsequently impart a ruffle thereto in a direction substantially perpendicular to the general direction of the sleeve.

16 Claims, 2 Drawing Sheets

RUFFLING SLIDE AND METHOD FOR MAKING SAME

BACKGROUND OF INVENTION

1. Field of Art

The present invention relates to articles made on the basis of fibrous sheets for which it is useful or necessary to be able to provide, by prior ruffling, a local functional zone of limited possible elastic stretching.

The term sheet should be considered to cover all supports or substrates based on natural and/or synthetic fibers arranged in a structured manner as obtained by weaving or organized at random like the non-woven supports or carded, even slightly needled, cloth. Articles corresponding to such characteristics are used in numerous areas, in particular for diapers.

2. Prior Art

It is generally desired to be able to have one or more ruffling portions available so that the portion in question may find a faculty of adaptation, conformation or retention compatible with the object or objects envisaged.

Up to the present time, it was desired to comply with such requirements by resorting to different methods employing each time one or more longitudinally elastic yarn element.

One of the known methods consists in connecting the longitudinally elastic yarn element with the substrate by means of a bead or dots of adhesion of an intermediate adhesive product.

Such a technique raises considerable problems in implementation, particularly in continuous production installations, as it is necessary to be able to have available a particularly precise regulation of temperature for the deposit of the bead or dots of adhesive product to be able to intervene with local precision, without overflow, without extrusion, without clogging of the dispensing installation and with the deposited quantity just necessary, all these requirements and conditions having to be able to be maintained constantly for relatively high speeds of manufacture of the articles.

It is apprecitaed that such a regulation of temperature for deposits of small quantity raises a virtually unsolvable problem for the present technique.

Another drawback of this technique resides in the fact that the adhesive product is more or less sensitive to dust which, by its presence may be such as to disturb the connection by adhesion between the elastic yarn element and the substrate.

Another drawback of this technique resides in the fact that the adhesive product may migrate in detrimental manner through the substrate, particularly in the case of laminating, giving the article produced an ineasthetic, even aggressive appearance, when the substrate is to be placed in direct relation with the epidermis. Such a migration may also be the source of a lamination detrimental to the local function having to be assumed. Such is the case of the fecal barriers of fitted diapers whose efficiency is ruined if these barriers no longer present, by adhesion on the support, the freedom necessary to be raised substantially perpendicularly to the plane of the support by the action of ruffling of the elastic yarn element.

Another technique of the prior art consists in connecting the elastic yarn element and the support by means of stitching made so as to traverse the elastic yarn element locally or to imprison the latter on the substrate.

This technique is not satisfactory for different reasons.

The cost of producing the ruffled portions becomes, in certain cases and in particular for much-consumed disposable articles, expensive due to the low speed of production, the expense generated by the consumption of the connecting elastic element and by the frequent interruptions due to the ruptures of the elastic yarn element, to the necessity of refilling the reels dispensing the elastic yarn element, even to the changes of the stitching heads by reason of ruptures or breaks of the needles.

A particularly crippling drawback of this technology also resides in the consequence resulting from the work of the needles which are led to traverse and therefore to perforate the substrate or substrates having to be filled.

Such perforations represent unsurmountable and difficult obstacles in the case of watertight articles having to be made, as is the case for certain scientific domains or for the medical domain.

In order to overcome the drawbacks of the techniques mentioned above, Patent Application FR 2 532 337 proposes another technique which consists of employing a ruffling slide comprising a tubular sleeve defined by the substrate and, for exampe, the fold of one of its edges. Inside this sleeve, between the two sheets, there is disposed an elastic yarn element which is connected to the walls of the sleeve by spaced apart transverse connecting portions, defining therebetween tubular ruffling portions, inside which the elastic yarn element is free. The connecting portions also ensure assembly of the two sheets of the sleeve together.

Such a ruffling slide is made continuously, by means of an installation disposing the sleeve placed flat, in the extended state and placing in the latter the elastic yarn element subjected to a longitudinal stretching stress. The installation then forms, by heat-sealing or high-frequency welding, locally and in aligned manner, the local immobilizations of the elastic yarn element on and between the two sheets of the sleeve. After execution of this immobilization, the stress on the elastic yarn element is released, with the result that it presents a length shorter than that of the tubular portion included between two immobilizations and it consequently imposes thereon a ruffling of orientation substantially perpendicular to the general direction of the sleeve.

This latter technique does in fact bring a solution to the problems raised by the other known techniques, but nonetheless presents certain drawbacks resulting from the very nature of the connecting portions employed.

In fact, in accordance with Application FR 2 532 337, the connecting portions, which present a substantially rectangular shape, simultaneously ensure a welding between the two sheets constituting the sleeve and an adhesion of the elastic yarn element on each of its two sheets, with the result that it is not possible to ensure adjustment of the ruffling after manufacture of the slide. Moreover, the connecting portions alter the behaviour of the elastic yarn element, creating discontinuities in its structure. These discontinuities result in particular from the mechanical and thermal stresses due to the operation of welding of the elastic yarn element on the walls of the sleeve. Similarly, the alteration of tubular portions in which the elastic yarn element is free and of connecting portions at the level of which the elastic yarn element adheres to the walls of the sleeve, does not make it possible to benefit fully from the mechanical characteristics of the elastic yarn element which is divided, to some extent, into a succession of independent elastic elements acting only at the level of one tubular portion to ruffle this latter.

SUMMARY OF THE INVENTION

It is precisely an object of the invention to improve the above technique by proposing a new technology capable of overcoming the drawbacks set forth above, which makes it possible to produce a water-tight ruffling slide, at low cost, with high capacity of stretching which may be produced in units or continuously. It is also an object of the invention to propose a technique for obtaining a novel product not requiring, when carried out, any particular arrangement for take-up at the level of the cuts made, with a view to stopping, by localized punctual connection, the longitudinally elastic yarn element with respect to the slide. The object of the invention is also to propose a novel technique which makes it possible to obtain a ruffling slide without altering the mechanical qualities of the elastic yarn element.

The object of the invention is to propose a novel technology of ruffling slide which offers capacities of stretching or reactivity adapted to the application envisaged, which may be produced at a low cost and at very high speed when the method carried out is that of continuous production and which may form the subject matter of an adjustment of the ruffling after manufacture.

In order to attain the objects set forth above, the ruffling slide comprises:
- a tubular sleeve intended to contain at least one elastic yarn element, connection portions which are arranged transversely in the sleeve, being spaced apart to define therebetween tubular ruffling portions and which effect local immobilizations of said elastic yarn element,
- at least one elastic yarn element disposed in the sleeve to be retained at the level of the immobilizations and to traverse freely and successively the tubular portions, presenting locally in each of them, on the one hand, its inoperative position and, or the other hand, a length less than that of the portion on which it subsequently imposes a ruffling of orientation substantially perpendicular to the general direction of the sleeve.

According to the invention, this ruffling slide is characterized in that each connecting portion defines a narrowed portion presenting a section of passage substantially close to that in the stretched state of the elastic yarn element, in order, on the one hand, to allow a relative displacement of the elastic yarn element under the effect of a so-called adjusting stress and, on the other hand, to immobilize the elastic yarn element when this latter is in inoperative position or subjected to a stress less than the adjusting stress.

The invention also has for an object the novel article comprising, integral therewith or added thereto, a ruffling slide according to the invention.

The invention also has for an object a method for obtaining the slide hereinabove, such a method consisting in:
- disposing a sleeve flat in the extended state,
- placing in the sleeve at least one elastic yarn element which is immobilized locally and which is subjected, furthermore, to a longitudinal stretching stress,
- locally making in the sleeve, in spaced apart manner, connecting portions:
  - which define in the sleeve tubular ruffling portions,
  - and which each effect an immobilization constituted by a narrowed portion presenting a section of passage substantially close to that of the stretched state of the elastic yarn element and retaining this latter, in order, on the one hand, to allow a relative displacement of the elastic yarn element under the effect of a so-called adjusting stress and, on the other hand, to immobilize the elastic yarn element when the latter is in inoperative position or subjected to a stress less than the adjusting stress,
- and releasing the stretching stress applied to the elastic yarn element which contracts to the inoperative position between the immobilizations and inside each tubular portion on which it imposes a ruffle.

Various other characteristics will appear from the following description with reference to the accompanying drawings which show, by way of non-limiting examples, forms of embodiment of the object of the invention.

DETAILED DESCRIPTION OF THE INVENTION

Figure 3:
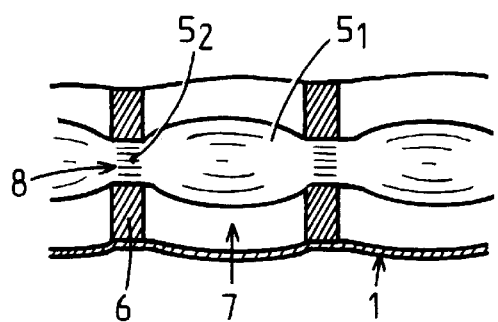
FIG. 3 is a partial section taken substantially along III—III of FIG. 1.
Figure 1:
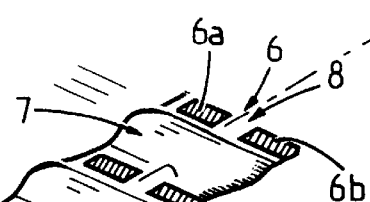
FIG. 1 is a partial perspective view illustrating the ruffling slide according to the invention.
Figure 2:
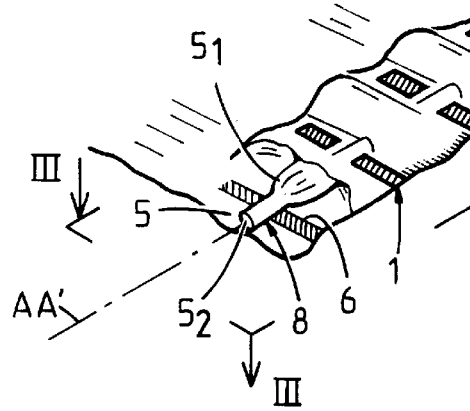
FIG. 2 is a partial perspective view showing, from another angle, another characteristic of the object of the invention.
Figure 2:
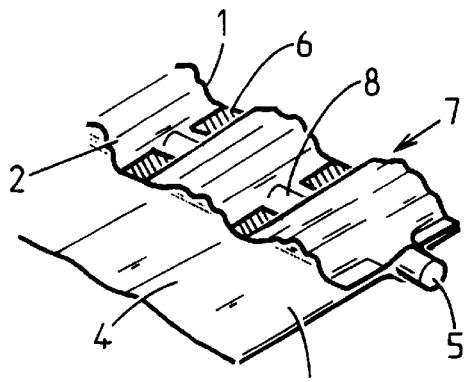

The ruffling slide according to FIGS. 1 to 3 is constituted from a fibrous substrate of any appropriate nature which may be woven or non-woven, and even, in certain cases, be constituted by a sheet or a continuous film of plastic material.

In the case of fibrous substrates, all suitable fibers or spun yarns of fibers may be retained and, more particularly, fibers which present per se or even by individual addition, a capacity of heat-sealing.

It may, of course, be envisaged to resort to substrates of fibers not intrinsically responding to this characteristic and, in such a case, a prior deposit may be made on the substrate by coating, spraying, immersion of a film of heat-sealable material.

The ruffling slide principally comprises a tubular sleeve 1 which may be considered as being made beforehand as such to constitute a unitary element, or be formed in situ, as a function of needs, as illustrated in FIG. 2. In such a case the sleeve is then formed by a fold or pleat 2 of a band 3 which may, if necessary and in certain applications, be consituted by the sheet having to present locally a character of stretchable ruffling. In such a case, the fold or pleat 2 is then formed by a sort of hem or edge established as selvedge of the sheet.

FIG. 2 also demonstrates that the fold or pleat 2 may be formed from a band to concern only a part of the width thereof, so as to allow a sort of projection 4 to exist, allowing, if necessary, a connection by stitching, adhesion or heat-sealing with a lap on which the projection must be added to fit the slide on said lap.

The sleeve 1 is intended to contain at least one elastic yarn element 5 elastically stretchable in the longitudinal direction and for example constituted by a mono- or multi-strand elastic yarn element, possibly covered.

By way of example and in the application to sanitary products such as fitted diapers, and even to mobcaps, the elastic yarn element 5 may advantageously be consittuted by a yarn of material sold on the market under the Trademark LYCRA®.

The elastic yarn element 5 is intended to be disposed inside the sleeve 1 which presents connecting portions 6 which are arranged transversely or inclined with respect to the longitudinal axis A–A' of said sleeve. Portions 6 are made spaced apart, equidistantly or not, so as to define therebetween and in the sleeve, successive elementary tubular ruffling portions 7. In the example illustrated, the connecting portions 6 are furthermore made so that each of them locally establishes an immobilization of the elastic yarn element 5. In the present case, such immobilization results from the fact that each connecting portion 6 is made so that the useful section of the sleeve 1 is limited to a narrowed portion 8 of which the passage is substantially close to the transverse cross section of the elastic yarn element 5 in the totally or partially stretched state. To that end, it may be considered that the portions 6 are each constituted for example by two tiles 6a and 6b which are arranged on either side of the longitudinal axis A–A' so as to form a narrowed portion 8. It must be considered that, according to the example of FIGS. 1 and 2, the axis A–A' is placed in median manner with respect to the width of the sleeve 1, but that a non-median position might also be envisaged. Similarly, the sleeve 1 might present a non-constant width.

The connecting portions 6 are made by any appropriate means so as to connect the two thicknesses constituting the sleeve 1 placed flat and spread out and for example a method employing heat-sealing may be considered as a solution offering considerable advantages.

It might be retained to make the connecting portions 6 so that the narrowed portion 8 is located, not in alignment with axis A–A' considered as median transversely speaking, but for example in relation with one of the edges of the sleeve corresponding to one of the folds of its structure placed flat or one of the folds formed by the pleat 2.

Preferably but not exclusively, the connecting portions 6 are made so that the narrowed portions 8 are aligned in rectilinear manner.

The above ruffling slide further comprises elastic yarn element 5 which is disposed inside the sleeve 1 so as to be retained at the level of the immobilizations 8 and to traverse the portions 7 freely and successively, but presenting its inoperative position such as $5_1$ inside each tubular portion.

An additional constructive arrangement employs an axial measurement of the elastic yarn element 5, included between two immobilizations 8, less in the inoperative position than the elementary length of each portion 7.

By reason of the relative anchoring which is established at the level of each immobilization 8 and by reason of this difference in length, the ruffling slide presents, in the inoperative position, a ruffle localized at the level of each tubular portion 7, as shown in FIG. 2. In this inoperative position, there is no possibility of relatively displacing the elastic yarn element 5 which is axially immobilized by the immobilizations 8 imprisoning by the narrowed portions the successive portions $5_2$ of the elastic yarn element 5.

However, it is possible to obtain, when an adjustment of the ruffling of the slide is desired, a relative axial displacement of the elastic yarn element 5 with respect to the immobilizations 8. To that end, there should be exerted on the elastic yarn element a so-called adjusting axial stress or traction, such that the dimensions of the transverse cross-section of the elastic yarn element 5 are smaller than those of the narrowed portions 8.

When the above sleeve is subjected to a stretching stress less than the adjusting stress, the portions $5_1$ of the elastic yarn element are stretched and allow the extension of each portion 7 without, however, provoking relative displacement of the elastic yarn element 5 on the axis A–A', being given the relative immobilization by the stretched zone $5_2$. When the elastic stretching stress ceases, the ruffling slide is stressed by the different portions $5_1$ which tend to resume their inoperative position and to reimpose the local ruffling of each portion 7. Moreover, by reason of the absence of dots of adherence between the sleeve 1 and the elastic yarn element 5, when the slide is subjected to a stretching stress, the whole length of the elastic yarn element participates in opposing the action of this stress, contrarily to what would happen in the case of a ruffling slide according to the prior art.

The ruffling slide, of the type described hereinabove, presents a particularly interesting advantage in the implementation when it constitutes more particularly, but not exclusively, an independent tubular element. In effect, by reason of the presence of the portions $5_1$ which, in the inoperative position, necessarily present a cross section greater than that of the immobilizations 8, a transverse cut to the desired length may be made to the sleeve without any regard nor any takeup operation. In effect, each cut end portion $5_1$ represents, by the cross section that it presents in the inoperative position, a stop maintaining the relation of tension existing between the elastic yarn element 5 and the sleeve 1 via the successive immobilizations 8 and portions 7.

It must, of course, be considered that the ruffling slide might comprise a plurality of alignments of immobilization 8, reserved for as many elastic yarn element 5 and that, in certain cases, it might also be envisaged to effect, for each alignment, immobilizations 8 which would not be made exactly in a rectilinear alignment, but might define, for an elastic yarn element 5, a path including more or less pronounced inflexions, and even alternate curves.

Figure 4:
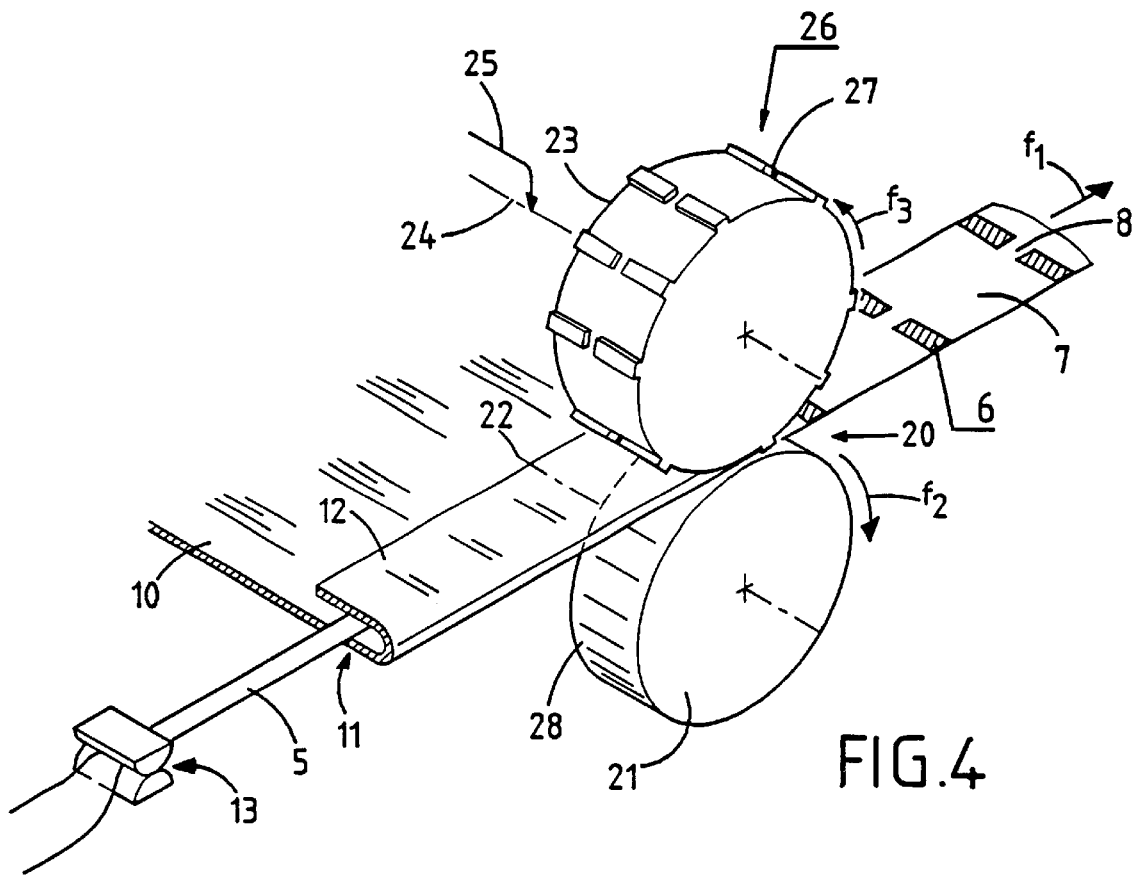
FIG. 4 is a schematic perspective view demonstrating a possibility of embodiment of the object of the invention.

FIG. 4 schematically illustrates an installation for carrying out a method for manufacturing the ruffling slide according to FIGS. 1 to 3. Such a method corresponds to an embodiment employing a sheet 10 from which a tube 11 is formed by an edge pleat 12 intended to constitute, directly on the sheet 10, the ruffling slide.

The means employed for ensuring the edge fold or pleat 12 do not come directly within the framework of the invention, as they must be considered as directly accessible to the man skilled in the art having to make, for example in textile matters, a continuous hem.

The formation of the sleeve 11 takes into account the insertion of a wire-like element 5 which is maintained between the layers constituting the fold or sleeve, being subjected to an elastic extension stress in the direction of arrow $f_1$, for example from a braking device 13, such as a wicket or gripping jaws limiting its free advance, so as to produce a tensioning upstream of a device 20 for forming the slide.

The sleeve 11 and the wire-like element 5 are obliged to advance in relation with the device 20 which comprises a duo of wheels of which one, for example 21, is called base or anvil and which is driven in rotation about its axis 22 passively or actively in the direction of arrow $f_2$. The duo 20 comprises another so-called forming wheel 23, driven in rotation in the direction of arrow $f_3$ about its axis 24 which is connected by any appropriate means to a source 25 capable of generating, locally and at the level of the gap between wheels, a connection between the thicknesses of substrate constituting the sleeve 11. The wheel 23 bears on its periphery positive impressions 26 which are constituted by axial bars presenting, for example in the transverse median plane, a notch 27 of which the width corresponds to the measurement of the narrowed portions 8 to be left. The bars 26 are organized in order successively to press the two thicknesses of matter against the wheel 21, so as to generate, locally, a rise in temperature promoting a local connection either from the fibers or from the coating of a heat-fusible product. Such heat-fusion may be provoked by direct heat application or via ultrasounds.

Although this has not been shown, the wheels 21 and 23 may be mounted relatively so that the bars 26 cooperate with the peripheral surface of the wheel 21 with or without pressure of application for example under the effect of an adjustable elastic stress.

The duo of wheels 20 is driven in synchronous rotation in the direction of the arrows, so as to provoke the advance in the direction of arrow $f_1$, simultaneously of sleeve 11 and the elastic yarn element 5 which is maintained in a state of stretch so that its transverse cross section is close by default to the width of the notches 27. Consequently, the rotation of the duo of wheels at the suitable speed produces on the sleeve 11, flat and in the extended state, the successively spaced apart connecting portions 6 defining therebetween the portions 7 and each forming a narrowed portion 8. Beyond or downstream of the device 20, the stretching stress imposed on the elastic yarn element ceases, with the result that this element re-adopts its inoperative position between two successive narrowed portions and produces the ruffling of the portion 7 concerned.

This method of manufacture presents the advantage, when producing the narrowed portions 8, of not welding the elastic yarn element to the sleeve and of not affecting the structure of said elastic yarn element whose mechanical characteristics are thus preserved.

It must be considered that a method of continuous production may be carried out for a tubular sleeve as unitary element previously provided with an elastic yarn element 5.

Similarly, the above arrangements are applicable to a method employing the provision of the slide with at least two independent elastic yarn elements.

Figure 6:
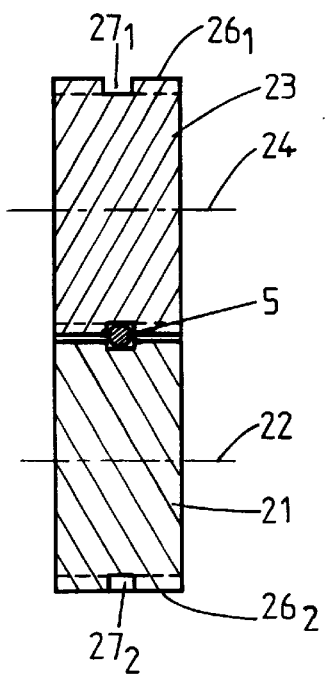
FIGS. 5 and 6 are schematic views showing different variant embodiments of the invention.
Figure 5:
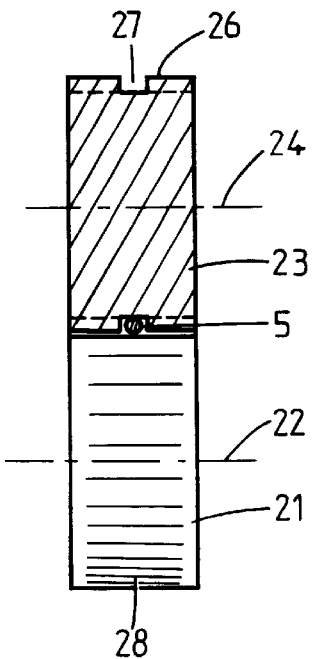

FIGS. 5 and 6 show two variant embodiments of the duo of wheels 21.

FIG. 5 corresponds to a transverse section of the example of FIG. 4 in which only the wheel 23 is equipped with bars 26, while the wheel 21 presents a smooth peripheral edge 28.

In the example according to FIG. 6, the two wheels 21 and 23 are provided on their periphery with bars $26_1$ and $26_2$ which are made to define therebetween and by the notches $27_1$ and $27_2$ that they form, each the half-section corresponding to the passage of the wire-like element 5. In such a case, the wheels 21 and 23 are then driven exactly at synchronous speed, so as each time to cause the bars $26_1$ and $26_2$ to come opposite in register, contributing to forming the connecting portions 6 and the immobilizations 8.

Figure 7:
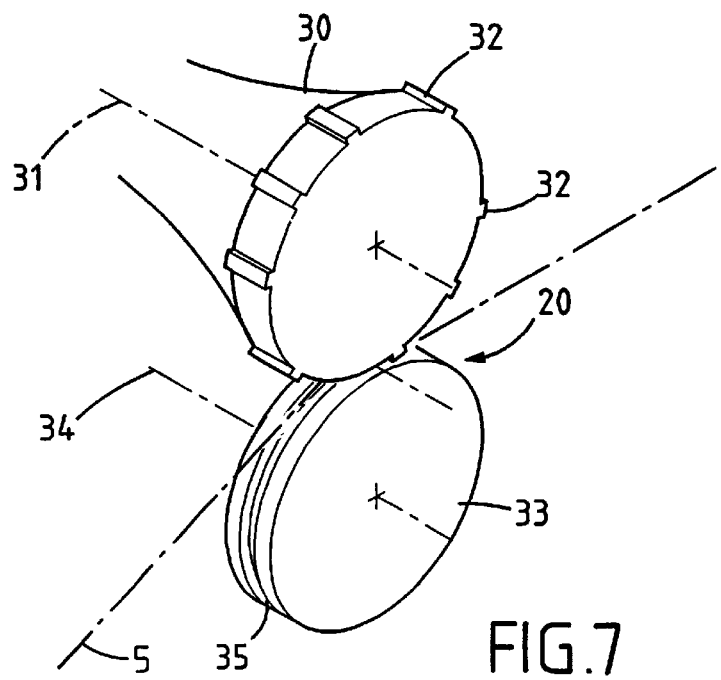
FIG. 7 is a schematic perspective view of an installation for making the slide according to FIG. 1.

FIG. 7 shows another schematic installation for carrying out a method for making the slide according to the invention. Such an installation comprises a device 20 which is composed of a sonotrode 30 rotating on its axis 31 and of which the periphery comprises, in places, bars 32 intended to produce the connecting portions 8. The device 20 also comprises an anvil wheel 33 rotating on its axis 34 and of which the periphery presents a continuous groove 35 whose width is slightly smaller than that of the elastic yarn element 5 in the stretched state.

The sleeve 11 is engaged between the sonotrode 30 and the wheel 33 so as to wind the elastic yarn element 5 locally in the gap between peripheral edges. Consequently, the elastic yarn element is correctly taken over and guided by the groove inside which it is completely engaged. In this way, upon each passage of a bar 32, the elastic yarn element is not affected by the high-frequency welding operation which forms the narrowed portions 8 and does not adhere to the sleeve 11.

Possibility of Industrial Application

The ruffling slide according to the invention may for example be employed on fitted diapers.

The invention is not limited to the embodiments described and shown, as various modifications may be made thereto without departing from its scope.

What is claimed is:

1. A ruffling slide comprising:
 a tubular sleeve having a plurality of connection portions being arranged transversely in the sleeve and spaced apart so as to define tubular ruffling portions, each of said connection portions having narrow portions; and
 at least one elastic yarn element inserted through said narrow portions, said at least one elastic yarn element being movable between a non-stretched mode in which said at least one elastic yarn element is arranged such that said narrow portions clamp and immobilize said at least one elastic yarn element wherein said at least one elastic yarn element imparts a ruffle to the sleeve in a direction substantially perpendicular to the general direction of the sleeve, and a stretched mode in which said at least one elastic element is released from said narrow portions.

2. The ruffling slide according to claim 1 wherein the connection portions are formed by heat sealing.

3. The ruffling slide according to claim 1 wherein the connection portions define a rectilinear path for the at least one elastic yarn element.

4. The ruffling slide according to claim 1 wherein the connection portions define a non-rectilinear path for the elastic yarn element.

5. The ruffling slide according to claim 1 wherein the connection portions define at least two paths for at least two elastic yarn elements.

6. The ruffling slide according to claim 1 wherein the sleeve represents an independent flat sheath.

7. The ruffling slide according to claim 6 wherein the sheath is formed by a pleat of a fibrous sheet.

8. The ruffling slide according to claim 1 comprising a tubular sleeve with a plurality of independent elastically stretchable yarn elements.

9. An article including a ruffling slide according to claim 1.

10. A method for producing a ruffling slide according to claim 1, said method comprising the steps of:
 arranging a tubular sleeve in a flat and extended position;
 inserting at least one elastic yarn element along said tubular sleeve;
 stretching said at least one elastic yarn element;
 immobilizing said at least one elastic yarn element;
 providing connection portions spaced transversely along said tubular sleeve so as to define tubular ruffling portions and narrow portions;
 releasing said at least one elastic yarn element so as to impart a ruffle to the tubular sleeve.

11. The method according to claim 10 wherein the connection portions define a rectilinear path for the at least one elastic yarn element.

12. The method according to claim 10 wherein the tubular sleeve is made by folding a portion of a sheet into an edge pleat.

13. The method according to claim 10 wherein the connection portions are formed by heat sealing.

14. A device for carrying out the method of claim 10 comprising:
- a forming device having two superposed peripherally engaged wheels driven in synchronous rotation;
- a feed mechanism arranged to pass a sheet including a tubular sleeve having at least one elastic yarn element inserted along said tubular sleeve through said wheels;
- a gripping device for tensioning said at least one elastic yarn element; and
- a plurality of bars located along a periphery and extending axially thereof of one of said two wheels.

15. The device according to claim 14 wherein one of said two wheels has a peripheral groove to accommodate said at least one elastic yarn element disposed within said tubular sleeve when said at least one elastic yarn element is in a stretched condition.

16. The device according to claim 15 wherein one of said two wheels comprises a welding wheel having said plurality of bars located along its periphery, the other of said two wheels comprises an anvil wheel having said peripheral groove.

* * * * *